United States Patent
Kriz et al.

(10) Patent No.: US 7,780,917 B2
(45) Date of Patent: *Aug. 24, 2010

(54) CALIBRATABLE FLOW DETECTOR

(75) Inventors: Dario Kriz, Höör (SE); Margareta Krook, Hjärup (SE)

(73) Assignee: Chemel AB, Lund (SE)

( * ) Notice: Subject to any disclaimer, the term of this patent is extended or adjusted under 35 U.S.C. 154(b) by 706 days.

This patent is subject to a terminal disclaimer.

(21) Appl. No.: 11/658,535

(22) PCT Filed: Jul. 25, 2005

(86) PCT No.: PCT/SE2005/001177

§ 371 (c)(1),
(2), (4) Date: Jan. 25, 2007

(87) PCT Pub. No.: WO2006/022579

PCT Pub. Date: Mar. 2, 2006

(65) Prior Publication Data

US 2008/0184810 A1 Aug. 7, 2008

(30) Foreign Application Priority Data

Aug. 25, 2004 (SE) .................................... 0402078

(51) Int. Cl.
*G01N 27/416* (2006.01)
*C12Q 1/68* (2006.01)
(52) U.S. Cl. ...................................... 422/82.01; 422/50
(58) Field of Classification Search ................. 204/409, 204/600; 73/61.57, 861.08
See application file for complete search history.

(56) References Cited

U.S. PATENT DOCUMENTS

| | | | | |
|---|---|---|---|---|
| 4,180,460 A | * | 12/1979 | Calari | 210/182 |
| 4,209,402 A | * | 6/1980 | Gentles | 210/137 |
| 4,668,396 A | * | 5/1987 | Baurmeister et al. | 210/500.29 |
| 4,834,882 A | * | 5/1989 | Kataoka et al. | 210/321.6 |
| 4,871,440 A | * | 10/1989 | Nagata et al. | 204/403.1 |
| 5,116,759 A | | 5/1992 | Klainer et al. | |
| 5,653,864 A | * | 8/1997 | Gotoh et al. | 205/777.5 |
| 5,733,442 A | * | 3/1998 | Shukla | 210/94 |
| 6,214,206 B1 | | 4/2001 | Kriz | |
| 6,287,438 B1 | * | 9/2001 | Knoll | 204/409 |
| 6,652,720 B1 | * | 11/2003 | Mansouri et al. | 204/403.11 |
| 6,706,160 B2 | | 3/2004 | Kriz | |
| 7,264,723 B2 | * | 9/2007 | Singh et al. | 210/321.6 |
| 2005/0147508 A1 | * | 7/2005 | Luongo et al. | 417/415 |
| 2005/0189225 A1 | * | 9/2005 | Liu et al. | 204/600 |
| 2008/0282780 A1 | * | 11/2008 | Kriz | 73/61.57 |

FOREIGN PATENT DOCUMENTS

| | | | |
|---|---|---|---|
| JP | 56-63261 A | * | 5/1981 |
| JP | 56 098488 A | | 8/1981 |
| JP | 02 208551 A | | 8/1990 |

OTHER PUBLICATIONS

JPO English language abstract of JP 56-63261 A Kunio et al.., patent published on May 29, 1981.*

* cited by examiner

*Primary Examiner*—Alex Noguerola
(74) *Attorney, Agent, or Firm*—Buchanan Ingersoll & Rooney PC

(57) ABSTRACT

A device and method are provided for the reliable calibration of detector units for the detection of low-molecular substances in a liquid flow.

16 Claims, 1 Drawing Sheet

CALIBRATABLE FLOW DETECTOR

This application is a 371 of PCT/SE2005/000911, filed on Jun. 15, 2005, which claims priority from Swedish application 0401814-9, filed on Jul. 8, 2004.

BACKGROUND

1. Field

Disclosed herein is to a device for quantitative and qualitative determination of chemical substances in a liquid flow from a micro-dialysis probe, filter unit, fermenter, cell suspension, chemical reactor, human being, tissue or animal.

The device can also act as a component in equipment for automatic regulation and control of chemical and/or biological processes in fermenters, cell suspensions and chemical reactors.

2. Description of Related Art

The annual world market for liquid chromatography has, from the beginning of the 1960s until today, grown extensively. The market leaders in this area are companies like Pharmacia & Upjohn AB, Applied Biosystems Inc, Bioanalytical Systems, Hitatchi Instruments and Waters Corporation.

In parallel with this development, tools such as micro-dialysis probes, have been produced for in vivo monitoring of patients and animals. Companies that are acting in this area include CMA Microdialys AB (Sweden) and SpectRx Inc (USA).

A third area involving monitoring and control of chemical processes and fermenters is under development. Companies that are active in this area are e.g. Applikon (NL), YSI Inc (USA) and Trace Biotech Ag (Germany). The latter company has. developed a micro-dialysis like device for sampling from a fermentor under sterile conditions.

The common point in the mentioned three areas is that they are all dependent on detection systems, which preferentially are of the type: a flow-through detector. Using different types of flow-through detectors several important chemical substances can be identified and quantified in different types of measuring matrices, exemplified but not limited to fermentation broths, blood, cerebrospinal fluid, urine etc.

Calibration of a flow—through cell is necessary to obtain accurate measuring results in qualitative and quantitative determination of chemical substances in liquid flows from micro-dialysis probes, filter units, fermenters, cell suspensions, chemical reacters, human beings, tissues and animals. The need for calibration originates from the effects on the measuring results from the flow—through cell emanating from either contamination caused by components in the matrix present in the mentioned liquid flow, and/or time dependent fluctuations of the composition of the liquid flow matrix. The latter fluctuations in the liquid flow matrix composition can arise as a result of chemical or biological processes in chemical reactors, fermenters, cell suspensions, and organisms like cells, tissue, human being, animal, plant, micro—organism or funghus.

It is already commonly known that calibration of chemical measuring equipment can be performed with a generally accepted procedure that goes by the name of the standard addition method, i.e. a known amount of the substance that is going to be analyzed is added to the sample solution to be analyzed. The procedure is based on the performance of a first measurement on the pure sample without any addition, followed by one (or more) new measurement (-s) on the sample now containing an addition of a known standard. The amount of the mentioned-substance can then be accurately calculated with mathematical methods.

The problem with this method is that it is cumbersome, time-consuming and demands substantial manual work.

Since 1995 a new type of biosensor technology, SIRE Biosensor, has been developed, which is based on the injection of recognition elements [SE 510 733 (1999), U.S. Pat. No. 6,214,206 (2001) & U.S. Pat. No. 6,706,160 (2004)]. This technology has solved many technological problems usually related to measuring of chemical substances.

SUMMARY

The devices and methods disclosed herein are advantageous because they can preferentially be integrated with the mentioned technology, since it can use injectable enzymes as reagents, but with the difference that it is based on a new technological construction, which solves problems that arise in qualitative and quantitative measurements of chemical substances in liquid flows, in a new and unexpected way.

So far few, technical solutions have been presented that in a powerful and automatable way solve the problems which arise in calibration of flow-through detectors.

The devices and methods disclosed herein solve the problems with calibration in a completely new way. The most important advantages with the devices and methods disclosed herein are, is in particular, that low molecular substances can be determined qualitatively and quantitatively with the reliably calibrated flow-through detector and that this detector can be joined in direct connection with a sample outlet.

In a particular embodiment disclosed herein is a device, containing a membrane that separates two flow-through chambers, where the first of the flow-through chambers contains a detector and an inlet and an outlet for a liquid flow, and the second flow-through chamber has a minimum of two inlets for liquid flows and a minimum of one outlet for a liquid flow.

Also disclosed herein, in a particular embodiment, is a method where a device described herein is used for calibration through standard addition, or alternatively through usual calibration, without the procedure for standard addition.

In a more particular embodiment is disclosed a method where a device described herein is especially used for quantitative and qualitative detection of substances in liquid flows in liquid chromatography (e.g. capillary LC, HPLC, FPLC, Affinity Chromatography and Gel Filtration), and for standard addition calibrated detection of low molecular substances exemplified but not limited to glucose, lactate, sucrose, ethanol, methanol, ascorbic acid, lactose, maltose, xnalic acid, citric acid or acetic acid in a liquid flow from a micro—dialysis probe, filter unit, fermenter, cell suspension, chemical reactor, human being, tissue or animal.

DETAILED DESCRIPTION OF SPECIFIC EMBODIMENTS

Figure 1:
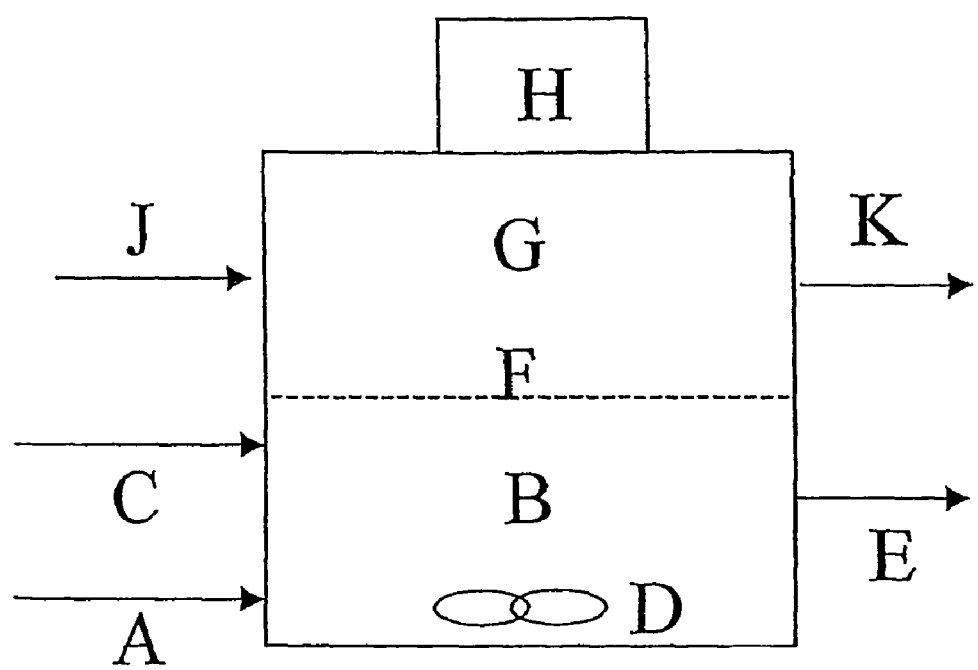
FIG. 1 shows a schematic diagram of an embodiment of device described herein.

A liquid flow containing the substance to be detected is guided through inlet A to flow-through chamber B. Through inlet C a liquid flow that contains only buffer solution, alternatively buffer solution with. a known amount of the substance to be determined. Both liquid flows are mixed in flow-through chamber B. The substance to be detected diffuses through the membrane F into flow-through chamber G where it can react with reagents, e.g. enzymes, that have been introduced to this chamber through inlet J. The substance or substrate/products that are consumed/produced in the enzymatic reaction generates a measuring signal when in contact with the detector H. The liquid in flow-through chamber G is let out through outlet K. The liquid in flow-through chamber B is let out through outlet E. Inlet J and outlet K in flow-through chamber G can be reversed so that flows run opposite to each other.

DETAILED DESCRIPTION OF THE INVENTION

According to one aspect of the invention, the device is characterized by that one and each of the flow-through chambers have a chamber volume interval of 0.1-5000

According to another aspect, the device is characterized by that the detector consists of an amperometric three-electrode system containing a working electrode made, of Platinum, a reference. electrode made of Silver and a counter electrode made of Platinum or Silver.

According to an additional aspect, the device according to the invention characterized by that the working electrode has a potential that lies +200 to +1000 mV above a Silver or Silver/Silver Chloride reference electrode potential.

According to an additional aspect of the invention, the received individual measuring signals from buffer, sample, sample added through standard addition, alternatively only standard, are used to calculate background compensated and calibrated quantitative and qualitative measuring results as defined by the SIRE Biosensor concept.

According to an additional aspect of the invention, the device is characterized by that it is equipped with a mixing unit D (FIG. 1) consisting of a magnetic rod or paddles, which are operated internally or externally by a mechanical motion or a rotating magnetic field.

According to an additional aspect of the invention, the device is characterized by that it is equipped with a heat-generating or cooling element for thermo control of the device to keep a constant temperature in the interval 5 to 80 degrees Celsius. This will among other things secure that fluctuations in the temperature of the surrounding area of the device will not affect the diffusion over the membrane F (FIG. 1) which in turn will affect the measuring signal.

According to an additional aspect of the invention, the device is characterized by that it is equipped with temperature sensor for mathematical compensation of the measuring' signal by software at temperature fluctuations.

According to one aspect the measuring principle is based on that the detector H (FIG. 3.) is a SIRE Biosensor mentioned earlier in this patent application.

FIG. 1 shows a schematic diagram of the device and method described herein. A liquid flow, e.g. 0.1 M phosphate buffer pH 7.4, containing the substance to be detected is guided through inlet A to flow-through chamber B. Through inlet C a liquid flow containing only buffer solution, alternatively a buffer solution containing a known amount of substance to be determined, e.g. 1 mM Glucose or Lactate. Both liquid flows are mixed in flow-through chamber B. The substance, e.g. Glucose, to be detected diffuses through the membrane F, e.g. a dialysis membrane (MWCO=3 kDa) made of cellulose acetate, into flow-through chamber G, where it can react with enzymes such as glucose oxidase or lactate oxidase, that has been introduced in liquid flows, e.g. 0.1 M phosphate buffer pH 7.4, through inlet J. The substance or the substrate/products that are consumed/produced by the enzymatic reaction generates an electrochemical or amperometric or optical measuring signal when in contact with the detector H. The liquid in flow-through chamber G is let out through outlet K. The liquid in flow-through chamber B is let out through outlet E. Inlet J and outlet K in flow-through chamber G can be reversed so that an. opposite flow is received.

The liquid flows through the flow-through chambers can e.g. be established by the use of pumps alternatively by self-act flow. Switching between different liquid flows containing a known substance alternatively enzymatic reagents is e.g. performed with external valves. Mixing of the different liquid flows that is introduced in flow-through chamber B can be done passively by diffusion, alternatively by laminar/turbulent flow, alternatively by stirring with a magnetic rod or a paddle.

By using more than two inlets to flow-through cell B, more than two different liquid flows be introduced in the mentioned flow-through cell independent of each other. This means that the number of external valves can be reduced and that different substances and different concentrations of the substance to be determined can be introduced into flow-through chamber B. Consequently, more than one substance can be analyzed. In addition, series (2-200) of measuring values for standard addition graphs are received resulting in more accurate measuring results.

The invention claimed is:

1. A biosensor device, comprising:
a first inlet, a second inlet, and a third inlet for fluid inflow;
a first outlet and a second outlet for fluid outflow;
a first flow-through chamber in fluid communication with the first inlet and the first outlet, and comprising an amperometric detector;
a second flow-through chamber separated from the first flow-through chamber by a semipermeable membrane, and in fluid communication with the second inlet, the third inlet and the second outlet; and
wherein one of the second and third inlets to the second flow-through chamber is connected to a liquid flow from a micro-dialysis probe, filter unit, fermenter, cell suspension, chemical reactor, human being, tissue, or animal.

2. A device according to claim 1, wherein said semi-permeable membrane contains nanopores with an average cross-section diameter in the interval 0.1-900 nm.

3. A device according to claim 2, wherein said semipermeable membrane consists of cellulose acetate, Nafion, ceramic material, metallurgic material or polymeric material.

4. A device according to claim 2, wherein said detector consists of a working electrode made of Platinum or another precious metal, a reference electrode made of Silver and a counter electrode made of Platinum.

5. A device according to claim 2, which is equipped with a heat generating or cooling source for thermostating of the device at a constant temperature in the range of 5 to 80 degrees Celsius.

6. A device according to claim 1, wherein said amperometric detector comprises a working electrode made of Platinum or another precious metal, a reference electrode made of Silver, and a counter electrode made of Platinum.

7. A device according to claim 6, which is equipped with a heat generating or cooling source for thermostating of the device at a constant temperature in the range of 5 to 80 degrees Celsius.

8. A device according to claim 1, further comprising a heat generating or cooling source for thermostatting of the device at a constant temperature in the range of 5 to 80 degrees Celsius.

9. A device according to claim 1, further comprising a valve with two or more inlets for injection of buffer solution, washing solution and calibration solution connected to one of the second or third inlets.

10. A device according to claim 1, wherein one of the inlets to the second flow-through chamber is connected to one or more liquid flows containing buffer solution, washing solution and calibration solution.

11. A device according to claim 10, wherein one of the inlets to the second flow-through chamber is connected to the outlet of a valve with two or more inlets for injection of buffer solution, washing solution and calibration solution.

12. A device according to claim 1, wherein the second flow-through chamber further comprises an internal mixing chamber therein, and wherein the second inlet and the third inlet are in fluid communication with, and conduct fluid inflow to the internal mixing chamber.

13. A device according to claim 1, wherein said the first flow-through chamber and the second flow-through chamber each have a chamber volume within the range of 0.1 to 5000 µl.

14. A method for the qualitative and/or quantitative determination of low-molecular weight (Mw<5 kDa) substances in a first liquid flow emanating from a micro-dialysis probe, filter unit, fermenter, cell suspension, chemical reactor, human being, tissue or animal comprising:
    introducing the first liquid flow to the second inlet of the biosensor device of claim 1;
    introducing a second liquid flow containing a buffer solution and optionally containing a known amount of a low-molecular weight substance to the third inlet of the biosensor device;
    introducing a liquid flow containing a reagent that reacts with one of the low-molecular weight substances introduced in the first liquid flow to the first inlet of the biosensor device;
    detecting a measurement signal generated with a reaction product of the reagent and low-molecular weight substance that has crossed the semipermeable membrane is in contact with the amperometric detector of the biosensor device;
    removing liquid from the first flow-through chamber from the first outlet of the biosensor device; and
    removing liquid from the second flow-through chamber from the second outlet of the biosensor device.

15. A method for optimisation, control or regulation of chemical or biological processes in fermenters, cell suspensions or chemical reactors comprising:
    qualitatively and/or quantitatively determining a low-molecular weight substance in a liquid flow according to the method of claim 14;
    optimizing, controlling, or regulating a fermenter, cell suspension or chemical reactor based upon the measurement signal obtained.

16. A device according to claim 1, wherein said amperometric detector comprises a working electrode made of Platinum or another precious metal, and a combined reference and counter electrode made of Silver/Silver Chloride.

* * * * *